United States Patent [19]

Sundeen et al.

[11] 4,173,649
[45] Nov. 6, 1979

[54] 5-PHENYL-2,4-PENTADIEN-1-AMINES AND METHOD FOR INHIBITING PROSTAGLANDIN DEHYDROGENASE

[75] Inventors: Joseph E. Sundeen, Yardley, Pa.; Tamara Dejneka, Skillman; Frederic P. Hauck, Bridgewater, both of N.J.

[73] Assignee: E. R. Squibb & Sons, Inc., Princeton, N.J.

[21] Appl. No.: 881,271

[22] Filed: Feb. 27, 1978

[51] Int. Cl.² .......... A61K 31/275; A61K 31/24; A61K 31/195; A61K 31/135
[52] U.S. Cl. .......... 424/304; 260/570.8 R; 424/309; 424/311; 424/319; 424/330
[58] Field of Search .......... 260/570.8 R; 424/330, 424/311, 304, 309, 319

[56] References Cited

U.S. PATENT DOCUMENTS 3,094,561  6/1963  Sundeen et al. .......... 424/330

OTHER PUBLICATIONS

Dimmock et al.-*J. of Pharm. Sci.*, vol. 63, #1, Jan. 1974, pp. 69–74; vol. 65, #4, Apr. 1976, 483–8.
Gschwend et al., *J. Org. Chem.* 38, 2169 (1973).
Peskar et al.-*J. Pharm. Pharmac.*, 1976, 28, 146.

*Primary Examiner*—Frederick E. Waddell
*Attorney, Agent, or Firm*—Lawrence S. Levinson; Burton Rodney

[57] ABSTRACT

5-Phenyl-2,4-pentadien-1-amines and salts thereof are provided having the structure

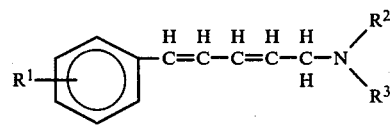

wherein $R^1$ is hydrogen, lower alkyl, lower alkoxy, hydroxy, lower alkanoyloxy, nitro, cyano, amino, carboxy or lower alkoxycarbonyl, and $R^2$ and $R^3$ are the same or different and are hydrogen, lower alkyl, alkenyl-lower alkyl, aralkyl, and substituted lower alkyl. These compounds possess useful pharmceutical activites due to their ability to inhibit the prostaglandin-inactivating enzyme 15-α-hydroxyprostaglandin dehydrogenase.

3 Claims, No Drawings

5-PHENYL-2,4-PENTADIEN-1-AMINES AND METHOD FOR INHIBITING PROSTAGLANDIN DEHYDROGENASE

BACKGROUND OF THE INVENTION

Dimmock et al, J. Pharmaceutical Sciences 65, 482 (1976) and 65, 69 (1974) disclose 5-dimethylamino-1-phenyl-1-penten-3-ones of the structure

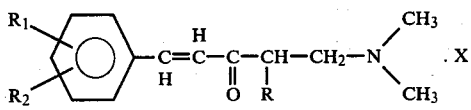

wherein $R_1$ and $R_2$ are H, or Cl, X is HCl or $CH_3I$ and R is H, $CH_3$ or $(CH_2)_4CH_3$ as inhibitors of mitochondrial function in yeast and inhibitors of blood platelet aggregation and as possessing antitumor properties.

Gschwend et al, J. Org. Chem. 38, 2169 (1973) in a paper entitled "Rates of Intramolecular Diels-Alder Reactions of Pentadienylacrylamides" disclose the synthesis of 4,5-diphenyl-2,4-pentadienylamines of the structure

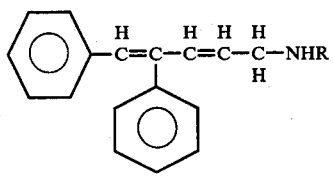

wherein R is H, $CH_3$, $C_2H_5$, i-$C_3H_7$ or t-$C_4H_9$ as well as N-alkyl-N-methyl-4,5-diphenyl-2,4-pentadienylamine.

DESCRIPTION OF THE INVENTION

The present invention relates to new 5-phenyl-2,4-pentadien-1-amines and to a method of employing such compounds in inhibiting prostaglandin dehydrogenase.

The 5-phenyl-2,4-pentadien-1-amines of the invention have the following structure

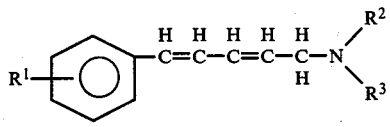

wherein $R^1$ is hydrogen, lower alkyl, lower alkoxy, hydroxy, lower alkanoyloxy, nitro, cyano, amino, carboxy or lower alkoxycarbonyl, and $R^2$ and $R^3$ may be the same or different and are hydrogen, lower alkyl, alkenyl-lower alkyl, aralkyl, and substituted lower alkyl, such as halo-lower alkyl, hydroxy-lower alkyl, lower alkoxy carbonyl-lower alkyl and cyano-lower alkyl, and physiologically acceptable salts thereof.

Preferred are those compounds of formula I wherein $R^1$ is hydrogen or halogen, for example 2-Cl, $R^2$ is methyl or ethyl and $R^3$ is methyl, ethyl or 2-propenyl.

Unless otherwise indicated the term "lower alkyl" or "alkyl" is employed herein includes both straight and branched chain radicals of up to eight carbon atoms, for instance, methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, and the like.

Unless otherwise indicated, the term "lower alkoxy" or "alkoxy" includes straight and branched chain radicals which correspond to the above lower alkyl groups attached to an oxygen atom.

Unless otherwise indicated, the term "lower alkanoyl" or "alkanoyl" as employed herein includes any of the above lower alkyl groups linked to a carbonyl group.

Unless otherwise indicated, the term "aralkyl" as employed herein contemplates monocyclic carbocyclic aryl radicals linked to a lower alkyl group as defined above, for instance, phenyl and substituted phenyl radicals, such as lower alkyl phenyl (e.g., o-, m- or p-tolyl, ethylphenyl, butylphenyl, and the like), halophenyl (e.g., chlorophenyl, bromophenyl, iodophenyl, fluorophenyl), linked to any of the lower alkyl groups.

The compounds of formula I of the invention are prepared by the Mannich reaction between a 4-phenyl-3-butene-2-one of the structure

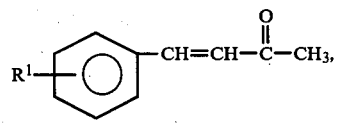

an amine of the structure,

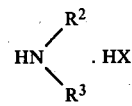

wherein X is Cl or Br, and paraformaldehyde under reflux and in the presence of an anhydrous alcohol in accordance with the procedure outlined in Dimmock et al, J. Pharmaceutical Science, 63, 69 (1974) and 65, 482 (1976), to form a 5-amino-1-phenyl-1-penten-3-one of the structure

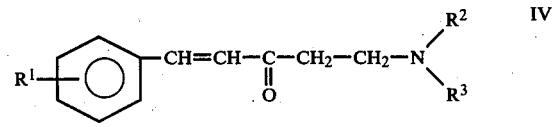

The compound of structure IV is then subjected to sodium borohydride reduction to form the 5-amino-1-phenyl-3-hydroxyl-1-pentene of the structure

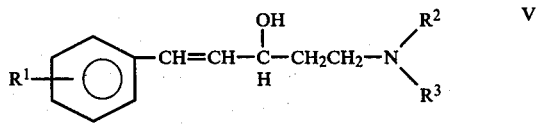

which is dissolved in acetic acid, optionally in the presence of a mineral acid, to form the formula I compounds.

Depending on the reaction conditions and the starting materials used, the compounds of formula I are obtained in the free form or in the form of their acid-addition salts. The salts thereof can be converted into the free compounds in a known manner such as by reaction with a basic agent. Free bases which may be obtained can be converted into pharmaceutically acceptable acid-addition salts by reaction with a variety of acids. Acids useful for preparing these acid-addition salts include, inter alia, inorganic acids, such as the hydrohalic acids (e.g., hydrochloric and hydrobromic acid), sulfuric acid, nitric acid, and phosphoric acid, and organic acids such as maleic, fumaric, tartaric, citric, acetic, benzoic, 2-acetoxybenzoic, salicyclic, succinic, nicotinic, methanesulfonic or cyclohexanesulfamic.

The compounds of this invention including their pharmaceutically acceptable salts have exhibited the ability to inhibit the action of 15-α-hydroxyprostaglandin dehydrogenase assayed according to the general procedure described by Anggard et al. (Methods In Enzymology, Vol. 14, pages 215–219 (1969)). Thus, the compounds of this invention are useful pharmaceutical agents possessing the ability to potentiate the pharmacological effects of exogenously introduced prostaglandins such as those of the F, E and A series, and to maintain adequate levels of endogenously produced prostaglandins. The compounds of this invention are additionally useful in the treatment of gastric ulcers and may be employed for that purpose in a manner similar to carbenoxolone (Peskar et al, J. Pharmacy and Pharmacology, 28, 146–148 (1976)).

A compound or mixture of compounds of formula I including their pharmaceutically acceptable salts can be administered orally or parenterally to various mammalian species in amounts ranging from about 10 to about 100 mg/kg/day divided into one or more doses for the pharmaceutical purpose set forth above. The compounds are formulated with an inert carrier according to conventional pharmaceutical practice. For example in the form of tablets, capsules, or an injectable solution.

The following Examples represent preferred embodiments of the present invention. All temperatures are expressed in degrees Centigrade.

EXAMPLE 1

N,N-Dimethyl-5-phenyl-2,4-pentadien-1-amine, hydrochloride

A. 5-(Dimethylamino)-1-phenyl-1-penten-3-one, hydrochloride (1:1)

trans-4-Phenyl-3-buten-2-one (14.6 g, 0.1 mole), dimethylamine hydrochloride (9.0 g, 0.1 mole) and paraformaldehyde (5.8 g, 0.2 mole) are heated at reflux in 150 ml of absolute ethanol for 3 hours. The reaction mixture is concentrated in vacuo, then washed with ether. Addition of ethyl acetate causes crystallization. The product is recrystallized from acetonitrile to yield 6.9 g, m.p. 150°–154° C.

B. 5-(Dimethylamino)-3-hydroxy-1-phenyl-1-pentene 5-(Dimethylamino)-1-phenyl-1-penten-3-one, hydrochloride (1:1) (18.6 g, 0.078 mole) is dissolved in 200 ml 1:1 methanol-water. Sodium bicarbonate (2.0 g) is added, followed by the portionwise addition of NaBH$_4$ (3.0 g) at 35° C. After addition, the reaction mixture is stirred for 2 hours at room temperature. This solution is diluted with 200 ml of water and organics are extracted with ether. The ether is dried with MgSO$_4$, filtered and concentrated in vacuo to yield 14.3 g of product. IR consistent.

C. N,N-Dimethyl-5-phenyl-2,4-pentadien-1-amine, hydrochloride (1:1)

The above material (from Part C) is dissolved in 40 ml of 37% aqueous HCl and 100 ml of glacial acetic acid. This solution is heated at reflux for 6 hours then concentrated in vacuo. The oil is washed with ether then ethyl acetate. The pasty solid is recrystallized from ethyl acetate-isopropanol (5:1) to yield 1.7 g of the title compound, m.p. 173°–177° C.

EXAMPLE 2

5-(2-Chlorophenyl)-N,N-dimethyl-2,4-pentadien-1-amine, hydrochloride (1:1)

A.

1-(2-Chlorophenyl)-5-(dimethylamino)-1-propen-3-one, hydrochloride (1:1)

A solution of 200 g (1.4 mole) of 2-chlorobenzaldehyde in 500 ml of acetone is treated with 200 ml of water, cooled in an ice bath, then treated with 40 ml of 10% NaOH by drops. The mixture is kept below 40° C. After the addition is complete the mixture is stirred at 25° C. for 1.5 hours, then acidified with 10% HCl. The mixture is diluted with water and extracted with benzene. 0.5 g of toluene-sulfonic acid is added to the benzene solution and the mixture refluxed under a water separator. A total of 6 ml of water is collected. The mixture is cooled, shaken with bicarbonate, dried (Na$_2$SO$_4$), and evaporated. Distillation gives 150 g (60%) of 4-(2-chlorophenyl)-but-3-ene-2-one, b.p. 106°–120° C. @ 1 mm Hg.

A mixture of 36 g (0.2 mole) of the above ketone, paraformaldehyde (12 g, 0.25 mole), and dimethylamine hydrochloride (17 g, 0.21 mole) in 300 ml of ethanol is refluxed for 2½ hours. Since the mixture is slightly cloudy, ½ ml of HCl in isopropanol is added, and the solution becomes clear and is refluxed another ½ hour. The solvents are removed in vacuo and the resulting solid triturated with ethyl acetate and filtered. Drying in vacuo gives 34 g (62%) of the crude Mannich base hydrochloride.

A 4 g sample is recrystallized from 50 ml of acetonitrile to give a white solid, m.p. 174°–175°.

B.

5-(2-Chlorophenyl)-N,N-dimethyl-2,4-pentadien-1-amine, hydrochloride (1:1)

A 30 g (0.11 mole) sample of 1-(2-chlorophenyl)-5-(dimethylamino)-1-propen-3-one, hydrochloride in 200 ml of methanol and 100 ml of water is treated with 8 g of sodium bicarbonate followed by 6 g of sodium borohydride in portions. After stirring for 2 hours, the mixture is diluted with water, extracted with ether, dried (Na$_2$CO$_3$) and evaporated. The crude oil is refluxed with 300 ml of acetic acid and 100 ml of concentrated HCl for 3 hours, then stripped to an oil. Trituration with ethyl acetate gives 9.6 g (34%) of solid diene hydrochloride.

Recrystallization of a 2 g sample from acetonitrile gives the title compound in the form of a white solid, 1.2 g, m.p. 175°–178°.

EXAMPLE 3

5-(2-Chlorophenyl)-N-methyl-N-2-propenyl-2,4-pentadien-1-amine, p-toluenesulfonate (1:1)

A. N-methyl-allylamine (JCS, 1479 (1950))

Benzaldehyde (89 g, 0.8 mole) is cooled in ice while treating with 46 g (0.8 mole) of allylamine. The mixture is allowed to warm to 25° C., ether (300 ml) is added and the water separated. Benzene (1 l.) is added, the cloudy mixture dried (Na$_2$SO$_4$) and evaporated to 600 ml. To this clear benzene solution is added 150 g (1.05 mole) of methyliodide and the mixture heated under slight pressure for 14 hours. Cooling and swirling gives a mass of solid which is filtered and washed with benzene. The solid is treated with warm water and the aqueous extracted with ether. The clear aqueous layer is basified with 50% NaOH and saturated with $Na_2CO_3$. The liberated base is extracted with ether, dried ($Na_2CO_3$), and distilled at 1 atm. The fraction boiling at 36° C. is discarded. The fraction with bp=37°-60° is treated with excess HCl in isopropanol, stripped to an oil, toluene added and evaporated to 8.5 g of a foam (0.08 mole). At 62°-64° a sample of pure amine is collected, 6 g (0.085 mole), for a total of 0.165 mole (20%) of amine.

B.
1-(2-Chlorophenyl)-5-(methyl-2-propenylamino)-1-penten-3-one, hydrochloride (1:1)

The 6 g sample of free base (of Part A) is converted to hydrochloride, combined with the other sample of hydrochloride, and heated with paraformaldehyde (9.8 g, 0.33 mole) and 4-(2-chlorophenyl)-3-buten-2-one (29 g, 0.16 mole) in 300 ml of absolute ethanol for 2½ hours. The clear solution is evaporated and dissolved in 300 ml of ethyl acetate. A sample of this solution is diluted with ether and scratched. The resulting solid is used to seed the ethyl acetate solution. The solid which crystallizes is filtered and dried in vacuo to give 32 g (66%) of Mannich base hydrochloride.

A 4 g sample is recrystallized twice from ether-acetonitrile to give 1.3 g of white solid, m.p. 136°-140° C.

C.
5-(2-Chlorophenyl)-N-methyl-N-2-propenyl-2,4-pentadien-1-amine

A 28 g sample of 1-(2-chlorophenyl)-5-(methyl-2-propenylamino)-1-penten-3-one, hydrochloride (0.093 mole) is dissolved in 200 ml of methanol and treated with 8 g of sodium bicarbonate dissolved in a minimum amount of water. To this mixture is added 6 g of sodium borohydride in portions. After stirring another 2 hours, water is added, and ether extraction gives 16 g of oil displaying no carbonyl in the IR spectrum. This material is refluxed for 3 hours with 100 ml of concentrated HCl and 300 ml of glacial acetic acid, then stripped to an oil and converted to the free base. This is partially soluble in hexane and is chromatographed in hexane on neutral alumina, Activity II.

D.
5-(2-Chlorophenyl)-N-methyl-N-2-propenyl-2,4-pentadien-1-amine, p-toluenesulfonate (1:1)

The fractions containing the least polar material (strongly UV active) are converted to 1.2 g of white hyrochloride (0.0042 mole) and 6.4 g (0.0152 mole) of white p-toluenesulfonic acid salt, for a total of 0.0194 mole (21%) of diene salt.

A 3.5 g sample of tosylate is recrystallized from ether-acetonitrile to give 2.7 g of the title compound in the form of a white solid, m.p. 118°-121°.

EXAMPLES 4 to 22

Following the procedure of Example 1 except substituting for trans-4-phenyl-3-butene-2-one, the compound shown in Column I of Table I below, and substituting for dimethylamine hydrochloride, the amine shown in Column II, the product shown in Column III is obtained.

TABLE I

| Ex. No. | Column I 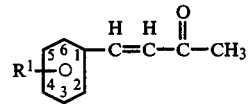 R$^1$ (position) | Column II 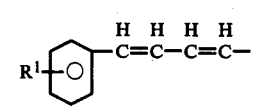 R$^2$ | R$^3$ | Column III  R$^1$ | R$^2$ | R$^3$ |
|---|---|---|---|---|---|---|
| 4. | H | $C_2H_5$ | $C_2H_5$ | as in Column I | as in Column II | |
| 5. | $CH_3$ (2) | H | H | | | |
| 6. | $C_2H_5$ (4) | H | $C_3H_7$ | | | |
| 7. | $CH_3O$ (2) | $C_2H_5$ | $CH_3$ | | | |
| 8. | $C_2H_5O$ (3) | $C_6H_5CH_2$ | $CH_3$ | | | |
| 9. | OH (2) | $CH_3$ | $CH_3$ | | | |
| 10. | OH (4) | $CH_3$ | $-CH_2-CH=CH_2$ | | | |
| 11. | $CH_3\overset{O}{\overset{\|}{C}}O$ (2) | $C_2H_5$ | $C_2H_5$ | | | |
| 12. | $C_3H_7\overset{O}{\overset{\|}{C}}O$ (4) | $C_6H_5CH_2$ | $C_6H_5CH_2$ | | | |
| 13. | $NO_2$ (3) | $-CH_2-CH=CH-CH_3$ | $-CH_2-CH=CH-CH_3$ | | | |
| 14. | $NO_2$ (2) | $Cl(CH_2)_3-$ | H | | | |
| 15. | CN (2) | H | $C_6H_5(CH_2)_2-$ | | | |
| 16. | CN (4) | $CNCH_2-$ | H | | | |
| 17. | $NH_2$ (2) | $CH_3O\overset{O}{\overset{\|}{C}}CH_2-$ | $CH_3O\overset{O}{\overset{\|}{C}}CH_2-$ | | | |
| 18. | $NH_2$ (4) | $CH_3$ | $C_2H_5$ | | | |
| 19. | COOH (2) | $-CH_3$ | $-CH_2-CH=CH_2$ | | | |
| 20. | COOH (4) | H | $C_2H_5$ | | | |
| 21. | $CH_3O\overset{O}{\overset{\|}{C}}$ (2) | $C_2H_5$ | $CH_3$ | | | |

TABLE I-continued

| | Column I | | Column II | | Column III | | |
|---|---|---|---|---|---|---|---|
| Ex. No. | $R^1$ (position) | | $R^2$ | $R^3$ | $R^1$ | $R^2$ | $R^3$ |
| 22. | $C_2H_5OC(4)$ with =O | | $CH_3$ | H | as in Column I | as in Column II | |

Column I structure: $R^1$-phenyl(positions 5,6,1,4,3,2)-CH=CH-C(=O)-CH$_3$
Column II structure: HN(R$^2$)(R$^3$)·HCl
Column III structure: $R^1$-phenyl-CH=CH-CH=CH-CH(H)-N(R$^2$)(R$^3$)

What is claimed is:

1. A pharmaceutical composition for use in treatment of gastric ulcers comprising a therapeutically effective amount of a compound of the structure

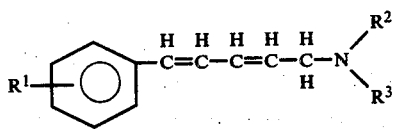

wherein $R^1$ is hydrogen, lower alkyl, lower alkoxy, halogen, hydroxy, lower alkanoyloxy, nitro, cyano, amino, carboxy or lower alkoxycarbonyl, and $R^2$ and $R^3$ may be the same or different and are hydrogen, lower alkyl, alkenyl-lower alkyl, phenyl-lower alkyl, lower alkylphenyl-lower alkyl, halophenyl-lower alkyl, halo-lower alkyl, hydroxy-lower alkyl, lower alkoxy carbonyl-lower alkyl and cyano-lower alkyl, and physiologically acceptable salts thereof and a pharmaceutically acceptable carrier therefor.

2. The method of inhibiting the enzyme 15-α-hydroxy prostaglandin dehydrogenase in a mammalian species by administering an effective amount of the composition of claim 1.

3. The method of treating gastric ulcers in a mammalian species by administering an effective amount of the composition of claim 1.

UNITED STATES PATENT AND TRADEMARK OFFICE
CERTIFICATE OF CORRECTION

PATENT NO. : 4,173,649
DATED : November 6, 1979
INVENTOR(S) : Joseph E. Sundeen, et al.

It is certified that error appears in the above-identified patent and that said Letters Patent are hereby corrected as shown below:

Column 8, Table I, Column III, the structure in the column heading should read

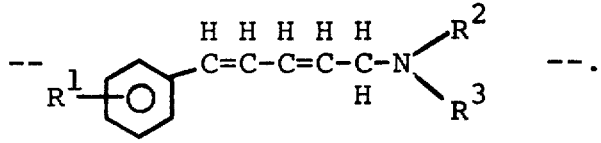

--.

Signed and Sealed this

First Day of April 1980

[SEAL]

Attest:

SIDNEY A. DIAMOND

*Attesting Officer*   *Commissioner of Patents and Trademarks*